United States Patent
Bashir-Hashemi et al.

(10) Patent No.: US 6,388,087 B1
(45) Date of Patent: May 14, 2002

(54) 3,3'-DINITRO-4,4'-HYDRAZOFURAZAN AND METHODS OF PREPARATION

(75) Inventors: Abdollah Bashir-Hashemi, Mission Viejo; Kurt Baum, Azusa, both of CA (US)

(73) Assignee: Fluorochem Inc., Azusa, CA (US)

( * ) Notice: Subject to any disclaimer, the term of this patent is extended or adjusted under 35 U.S.C. 154(b) by 0 days.

(21) Appl. No.: 09/718,947

(22) Filed: Nov. 21, 2000

(51) Int. Cl.⁷ .............................................. C07D 271/08
(52) U.S. Cl. ....................................................... 548/125
(58) Field of Search ......................................... 548/125

(56) References Cited

PUBLICATIONS

Beal, Propellonts, Explosives, pyrotechnics 25, 241–6 2000.*
Solidyuk, G.D.; Boldyrev, M.D.; Gidaspov, B.V.; Nikolaev, V.D. Zhur. Org. Khim. 1981 17(4), 861–5.
Kulagina, V.O.; Novikova, T.S.; Mel'nikova, T.M.; Khmelnitskii, L.I. Chem. Heterocyclic Comp. 1994, 30(5), 631–5.
Kulagina, V.O.; Novikova T.M,; Khmelnitskii, L.I. Chem. Heterocyclic Comp. 1994, 30(5), 629–30.
Sheremetev, A.B.; Kulgna, V.O.; Aleksandrova, N.S.; Dmitriev, D.E.; Strelenko, Y.A.; Lebedev, V.P.; Matyushin, Y.N. Propellants, Explosives, Pyrotechnics, 1998, 23, 142–9.
Chavez, D.; Hill, L.; Hiskey, M.; Kinkead, S.J. of Energetic Materials, vol. 18, p. 219–236 (2000).
March, J., "Advanced Organic Chemistry", McGraw–Hill Book Co., New York, N.Y., 1977, p 1125–1132.
pGunasedavan, A.; Trudell, M.L.; Boyer, J.H. Heteroatom Chem. 1994, 516, 441.
Zelenin, A.K.; Stevens, E.D. Trudell, M.L.; Structural Chemistry 1997, 8(5), 373.

* cited by examiner

Primary Examiner—Robert Gerstl
(74) Attorney, Agent, or Firm—Joseph E. Mueth

(57) ABSTRACT

The novel compound 3,3-Dinitro-4,4'-hydrozofurazan and the methods of preparation. The method of preparation 3,3-Dinitro-4,4'-hydrazofurazan which comprises partially reducing 3,3'-Dinitro-4,4'-azoxyfurazan. The method of preparing 3,3'-Dinitro-4,4'-hydrazofurazan by the partial reduction of 3,3'-Dinitro-4,4'-azofurazan.

7 Claims, No Drawings

3,3'-DINITRO-4,4'-HYDRAZOFURAZAN AND METHODS OF PREPARATION

BACKGROUND OF INVENTION

Furazan derivatives have been of interest for the construction of rocket propellants and explosives ingredients because the compounds are relatively insensitive and yet provide favorable oxygen balance. The starting point is usually diaminofurazan, and oxidation converts amino groups to nitro groups, and also to azo and azoxy groups. The azo and azoxy groups serve as energetic linking groups that link two or more furazan rings: Solidyuk, G. D.; Boldyrev, M. D.; Gidaspov, B. V.; Nikolaev. V. D. Zhur.Org.Khim. 1981 17(4), 861–5. Kulagina, V. O.; Novikova, T. S.; Mel'nikova, T. M.; Khmelnitskii, L. I. Chem. Heterocyclic Comp. 1994, 30(5), 631–5. Kulagina, V. O.; Novikova, T. M.; Khmelnitskii, L. I. Chem.HeterocyclicComp. 1994, 30(5), 629–30. Sheremetev, A. B.; Kulgina, V. O.; Aleksandrova, N. S.; Dmitriev, D. E.; Strelenko, Y. A.; Lebedev, V. P.; Matyushin, Y. N. Propellants, Explosives, Pyrotechnics 1998, 23,142–9.

The use of reduction chemistry to modify the structures of furazans has been little studied. It has recently been reported that the reduction of 3,3'-diamino-4,4'-azoxyfurazan with zinc in acetic acid gave 3,3'-diamino-4,4'hydrazofurazan, which could be oxidized to the desired 3,3'-diamino-4,4'-azofurazan with air. Chavez, D.; Hill, L.; Hiskey, M.; Kinkead,S. J. of Energetic Materials, Vol.18, p. 219–236 (2000). Selective reductions of azoxy groups in the presence of nitro groups are not trivial. Thus, March J., "Advanced Organic Chemistry", McGraw-Hill Book Co., New York, N.Y., 1977, p. 1125–1132 reported that nitro groups and azoxy groups are both reduced by zinc/acid.

SUMMARY OF INVENTION

This invention relates to the novel compound 3,3-Dinitro-4,4'-hydrazofurazan and the methods of preparation.

One method of preparing 3,3-Dinitro-4,4'-hydrazofurazan comprises partially reducing 3,3'-Dinitro-4,4'-azoxyfurazan.

Another method of preparing 3,3'-Dinitro-4,4'-hydrazofurazan according to this invention is by the partial reduction of 3,3'-Dinitro-4,4'-azofurazan.

UTILITY 3,3'-Dinitro-4,4'-hydrazofurazan is valuable as an ingredient for rocket propellants and explosives because of its combination of high oxygen balance, high melting point, and low sensitivity to impact and friction.

DESCRIPTION OF PREFERRED EMBODIMENTS

It was found in the present invention that selective reductions of furazan derivatives to yield 3,3'-Dinitro hydrazofurazan can be carried out if a mild reducing agent is used, and the amount of the reducing agent is restricted. In one embodiment, the partial reduction of 3-amino-3 nitro-4,4'-azoxyfurazan I with $Zn/CH_3COOH$ gave 3,3'-dinitro-4,4'-hydrazofurazan (DNHF) II, along with 3,3'-dinitro-4,4'-azofurazan III and 3,3'-diamino-4,4'-azoxyfurazan IV as depicted by the following reaction equation:

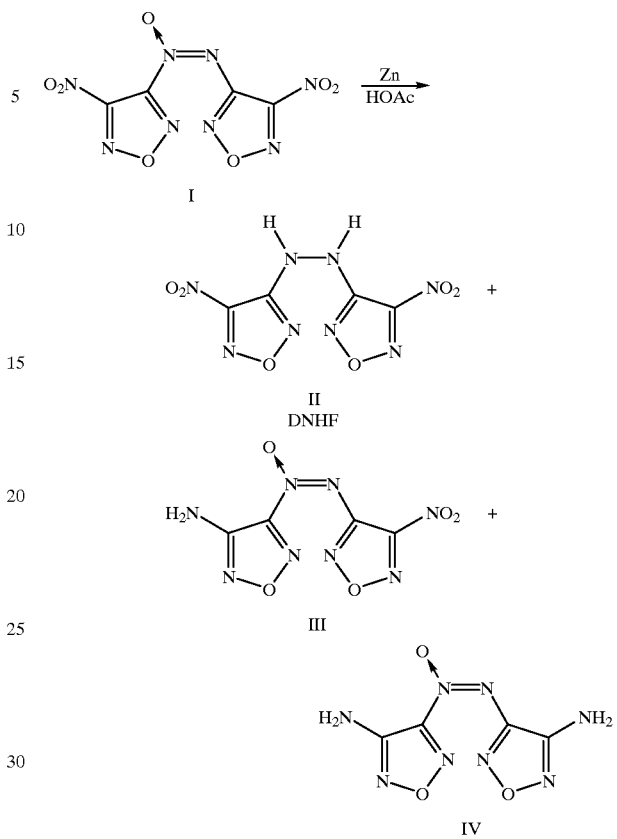

Differential scanning calorimetry (DSC) showed a melting point of 176° C., and decomposition beginning at 224° C. Impact sensitivity tests, conducted at Edwards Air Force Base, gave negative results at 200 cm, the highest setting of the machine. Friction sensitivity was 19.2 kg, compared to 5.0 kg for CL20, the most energetic explosive in production. X-ray crystallography, conducted by the Naval Research Laboratory, showed that the density of 3,3'-Dinitro-4,4'-hydrazofurazan is 1.78 g/cc.

Example 1 to 3 illustrate the reaction depicted above.

EXAMPLE 1

3,3'-Dinitro-4,4'-hydrazofurazan,DNHF

To a suspension of compound (I)(1.5 g, 5.5 mmol) and Zn (1.8 g, 27 mmol) in 30 ml of MeOH at room temperature, was added dropwise glacial acetic acid (1.8 ml, 30 mmol). A vigorous reaction occurred, and after the greenish reaction mixture was stirred at room temperature for 3 h, the mixture was filtered through a bed of celite and the filtrate was concentrated on a rotary evaporator. The residue was triturated with acetone (10 ml) and the acetone solution was concentrated. Column chromatography of the reaction product on silica gel using $CH_2Cl_2/EtOAc(4:1)$ gave four materials. The first product eluted was a reddish solid, identified as the starting material, 3,3'-dinitro-4,4'-azoxyfurazan, pGunasekavan, A.; Trudell, M. L.; Boyer, J. H. Heteroatom Chem.1994,516,441. (I), mp 110–112° C. (20 mg).

EXAMPLE 2

The second product was recrystallized from chloroform/acetone to give (840 mg, 60% yield) of 3,3'-dinitro-4,4'-hydrazofurazan (II), a pale yellow solid, mp. 173–175° C.: $^1H$ NMR (DMSO-$d_6$/CDCl$_3$) δ8.89 ppm (s); $^{13}C$ NMR (DMSO-$d_6$/CDCl$_3$) δ157.54, 151.88 ppm; IR (nujol) 3369.7, 2924, 1622, 1528, 1441 and 837.9 cm$^{-1}$. Anal. Calcd for $C_4H_2N_8O_6$; C, 18.68; H, 0.76; N, 4340. Found: C, 18.73; H, 0.74; N, 42.86. Compound II was soluble in acetone, methanol and ethyl acetate and slightly soluble in methylene chloride, ether and chloroform.

EXAMPLE 3

The third compound was identified in Zelenin, A. K.; Stevens, E. D.; Trudell, M. L., *Structural Chemistry* 1997, 8 (5), 373 as 3-amino-3'-nitro-4,4'-azoxyfurazane (III) (35 mg, 3%): mp 130–132° C.; $^1$H NMR (DMSO-$d_6$) δ7.14 ppm(s). The fourth product was identified[8] as 3,3'-diamino-4,4'-azoxyfurazane (IV), (300 mg, 25%): mp 245–248° C.; $^1$H NMR (DMSO-$d_6$) δ6.95 (s), 6.69 ppm (s).

The Synthesis of 3,3'-Dinitro-4,4'-hydrazofurazan From 3,3'-Dinitro-4,4'-azofurazan The partial reduction of 3,3'-dinitro-4,4'-azofurazan with Zn/CH$_3$COOH gave 3,3'-dinitro-4,4'-hydrazofurazan in quantitative yield. No additional purification by column chromatography was needed for this reaction, in contrast to the reaction based on 3,3'-dinitro 4,4'-azoxyfurazan. The synthesis of the starting material, 3,3'-dinitro-4,4'-azofurazan has been reported by the oxidation of a mixture of diaminofurazan and 3-amino-3'-nitro-4,4'-azoxyfurazan with permanganate. (Strelenko Y. A., et al, supra). The reaction is shown by the following equation:

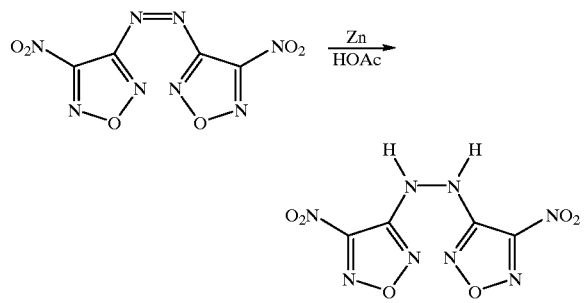

EXAMPLE 4

Synthesis of 3,3'-Dinitro-4,4'-hydrazofurazan From 3,3'-Dinitro-4,4'-azofurazan

To a suspension of 3,3'-dinitro-4,4'-azofurazan (1.42 g, 6.0 mmol) and Zn (0.78 g, 12 mmol) in 10 ml of methanol at room temperature, was added dropwise glacial acetic acid (0.8 ml, 12 mmol). A vigorous reaction took place, and after the greenish reaction mixture was stirred at room temperature for 2 hours. The slurry was filtered through a bed of celite and the filtrate was concentrated on a rotary evaporator and passed through a bed of silica gel using CH$_2$Cl$_2$/EtOAc. Removal of solvent gave 1.46 g (100% yield, one spot by TLC) of 3,3'-dinitro-4,4'-hydrazofurazan, a pale yellow solid, $^1$H NMR(DMSO-$d_6$); δ9.98 (s) ppm. Recrystallization from chloroform/acetone gave 1.26 g of 3,3'-dinitro-4,4'-hydrazofurazan, mp 171–173° C.

The zinc-glacial acetic acid combination is a preferred reducing agent. However, any reducing agent that can reduce an azo or azoxy group to a hydrazine can be used. If the strength of the reducing agent is such that it does not also reduce nitro groups, the amount of reducing agent used is immaterial. If a stronger reducing agent is used, the amount of reducing agent used should be minimized so that at least a portion of the 3,3'-Dinitro-4,4'-hydrazofurazan formed does not undergo further reduction at the nitro groups. In the azoxy Examples 1 to 3, byproducts resulting from nitro reduction were evident.

In most reductions, higher temperatures up to about 100° C. or more make the reactions faster but less selective, minimizing nitro reduction. Going to 0° C. can be beneficial. Even lower temperatures, such as going to dry ice temperature, would slow the reaction to an impractical rate.

In the Examples, the starting material and zinc were dissolved or suspended in methanol, and acetic acid was added slowly, starting at room temperature. When about half of the acid had been added, a vigorous reaction set in, bringing the methanol to reflux temperature.

There are many combinations of reducing agents and solvents that are in common usage. Some examples are hydrogen with platinum or palladium catalysis; sodium borohydride in alcohols; lithium aluminum hydride in ether, tin in hydrochloric acid.

The following are the claims.

What is claimed is:

1. The novel compound 3,3-Dinitro-4,4'-hydrazofurazan and the methods of preparation.
2. The method of preparation 3,3-Dinitro-4,4'-hydrazofurazan which comprises partially reducing 3,3'-Dinitro-4,4'-azoxyfurazan.
3. The method of claim 2 wherein the reduction is carried out with zinc and glacial acetic acid.
4. The method of claim 3 wherein the reduction is carried out at room temperature.
5. The method of preparing 3,3'-Dinitro-4,4'-hydrazofurazan by the partial reduction of 3,3'-Dinitro-4,4'-azofurazan.
6. The method of claim 5 wherein the reduction is carried out with zinc and glacial acetic acid.
7. The method of claim 6 wherein the reduction is carried out at room temperature.

* * * * *

UNITED STATES PATENT AND TRADEMARK OFFICE
CERTIFICATE OF CORRECTION

PATENT NO.    : 6,388,087 B1
DATED         : May 14, 2002
INVENTOR(S)   : Bashir-Hashemi et al.

It is certified that error appears in the above-identified patent and that said Letters Patent is hereby corrected as shown below:

<u>Title page,</u>
Item [75], please insert inventor -- Francisco Q. Roberto --

Signed and Sealed this

Twelfth Day of November, 2002

Attest:

Attesting Officer

JAMES E. ROGAN
*Director of the United States Patent and Trademark Office*